United States Patent [19]

Blough, Jr.

[11] Patent Number: 4,889,611
[45] Date of Patent: Dec. 26, 1989

[54] FLOW CELL
[75] Inventor: William M. Blough, Jr., Brea, Calif.
[73] Assignee: Beckman Instruments, Inc., Fullerton, Calif.
[21] Appl. No.: 277,477
[22] Filed: Nov. 23, 1988

Related U.S. Application Data

[63] Continuation of Ser. No. 50,844, May 15, 1987, abandoned.

[51] Int. Cl.[4] .................................... G01N 27/26
[52] U.S. Cl. ............................... 204/411; 204/412; 204/416; 204/419; 204/420
[58] Field of Search ............ 204/409, 412, 416, 418, 204/419, 420

[56] References Cited

U.S. PATENT DOCUMENTS

| | | | |
|---|---|---|---|
| 2,563,062 | 8/1951 | Perley | 204/195 |
| 3,649,504 | 3/1972 | Evans et al. | 204/195 |
| 3,862,895 | 9/1975 | King et al. | 204/295 |
| 3,997,420 | 12/1976 | Buzza | 204/195 P |
| 4,003,705 | 1/1977 | Buzza et al. | 23/230 R |
| 4,149,950 | 4/1979 | Potts | 204/195 G |
| 4,170,523 | 10/1979 | Buzza et al. | 204/1 T |
| 4,171,253 | 10/1979 | Nolan et al. | 204/412 |
| 4,360,415 | 11/1982 | Brezinski | 204/195 F |
| 4,440,619 | 4/1984 | Daroczy et al. | 204/401 |
| 4,490,234 | 12/1984 | Buzza | 204/409 |
| 4,506,226 | 3/1985 | Luce et al. | 324/459 |
| 4,531,088 | 7/1985 | Czaban et al. | 204/411 |
| 4,596,649 | 6/1986 | Hofmeier et al. | 204/411 |
| 4,604,166 | 8/1986 | Weinberg et al. | 204/1 T |
| 4,605,473 | 8/1986 | Dewald | 204/1 T |

FOREIGN PATENT DOCUMENTS

| | | | |
|---|---|---|---|
| 0094677 | 5/1983 | European Pat. Off. | 27/28 |
| WO83/03005 | 9/1983 | Finland | 27/40 |

OTHER PUBLICATIONS

Beckman System E4A TM Operating Manual (015-556855-A) pp. 3-1 through 3-8, 1982.

Primary Examiner—John F. Niebling
Assistant Examiner—Kathryn Gorgos
Attorney, Agent, or Firm—William H. May; Arnold Grant; Gary T. Hampson

[57] ABSTRACT

An ion selective electrode flow cell includes a first fluid conduit and at least two ion sensing electrodes each having ion sensing surfaces disposed within the first fluid conduit. A second fluid conduit and an ion sensing electrode having an ion sensing tip is disposed within the second conduit. There is an electrically conducting bridge connecting the first and second fluid conduits. A conductive member is disposed within the first fluid conduit proximate the ion sensing surfaces of two ion sensing electrodes and the bridge. A third fluid conduit may intersect the first fluid conduit and can include grounding for grounding fluid flowing through the third fluid conduit. Capacitors between exit and entry ports of the first and second fluid conduits and ground reduce electrical noise within the flow cell.

17 Claims, 2 Drawing Sheets

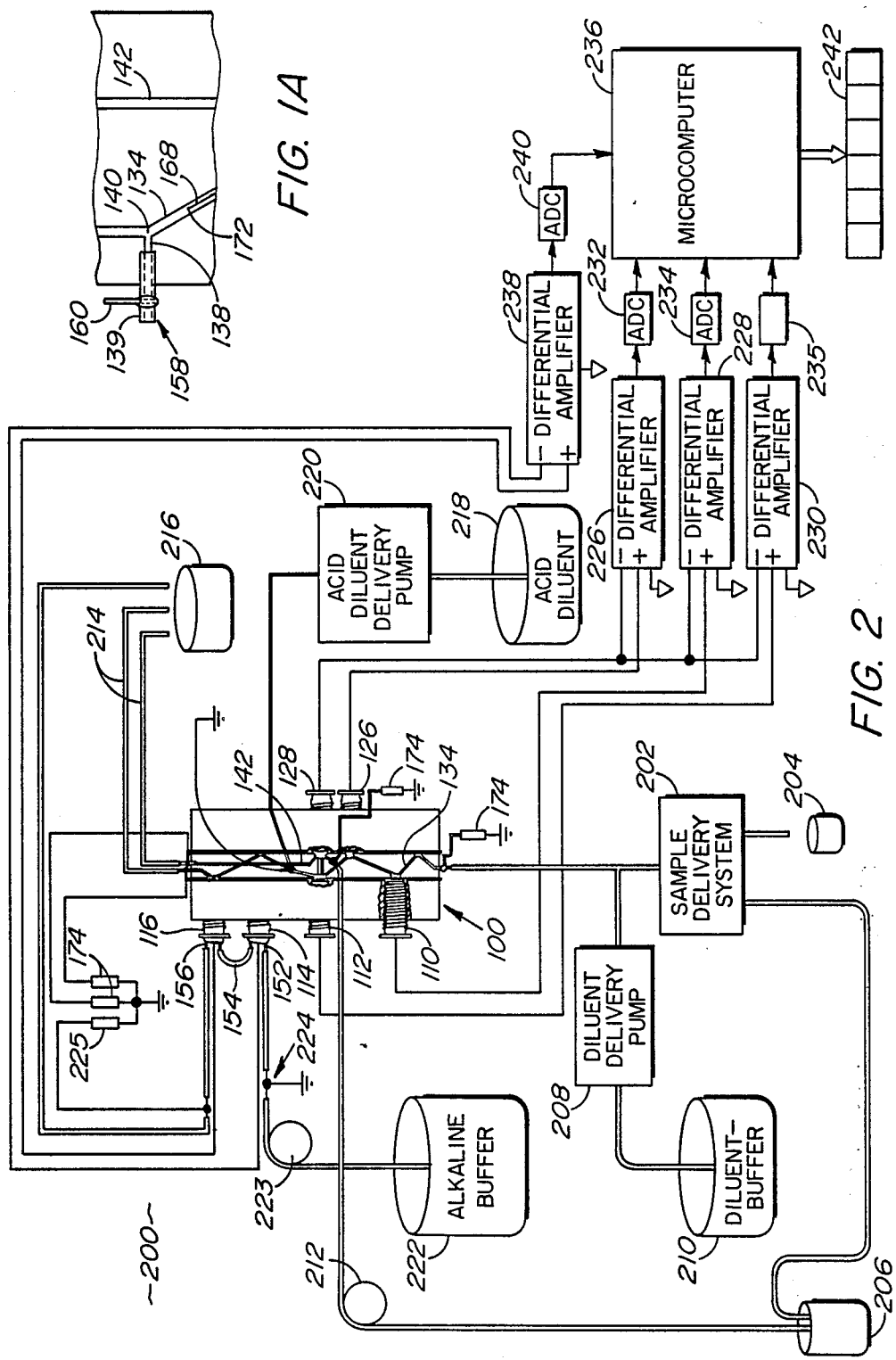

FLOW CELL

This is a continuation of co-pending application Ser. No. 050,844 filed on May 15, 1987, now abandoned.

FIELD OF THE INVENTION

The present invention relates generally to the field of electrochemistry and more particularly to an improved multi-electrode flow cell exhibiting improved noise suppression and cancellation characteristics.

BACKGROUND OF THE INVENTION

Fluid flow cells incorporating ion selective electrodes arranged to measure the ionic activity of fluids flowing through such cells are well known in the art. For example, the System E4A ™ Electrolyte Analyzer available from Beckman Instruments, Inc., Brea, Calif. 92621 incorporates such a fluid flow cell. In simplified form, the flow cell includes a body through which are formed a reference solution conduit and sample fluid conduit. The reference solution conduit conducts a reference solution past an electrochemically active surface of a compensating electrode. Similarly, the sample fluid conduit conducts a sample fluid stream past electrochemically active surfaces of respective ion selective electrodes. A low impedance salt bridge near the compensating electrode electrically connects the reference solution conduit to the sample fluid conduit.

The ion selective electrodes in the sample fluid conduit measure the concentrations of ions in the sample fluid in proportion to the concentration of certain electrolytes, such as, for example, sodium, potassium, and chloride. The purpose of the compensating electrode is to provide a compensating signal which varies with respect to environmental changes and influences, such as temperature changes and electrical noise, to which all of the ion selective electrodes are subjected.

The E4A flow cell further includes an acid diluent conduit which intersects the sample fluid conduit on the downstream side of the salt bridge so as to combine the sample fluid with an acid diluent. The resulting diluted sample mixture flows past another electrode which is one of a pair used to measure $CO_2$ concentrations.

The E4A flow cell is part of a fluid system within the analyzer that includes fluid reservoirs, fluid conduits, pumps and pinch valves. Unfortunately, the fluid paths defined by the fluid system leading to and from the flow cell act as antennas, causing potentially interfering electrical signals induced in such paths to be conducted into the flow cell and detected by the ion selective electrodes. In order to reduce such interference, the E4A analyzer includes electrostatic or Faraday shielding around the cell and a portion of the connecting fluid paths as well as grounding bypass capacitors connected to the outlets of the fluid reservoirs. Also, a solution ground, place at the flow cell entry port of the reference solution conduit, serves in part to ground noise which may enter the flow cell.

Although the E4A analyzer interference reduction techniques just described have proven to be sufficient, such techniques have been found to be ineffective or overly burdensome where the E4A flow cell is used in a physically larger instrument. For example, Faraday shielding becomes very difficult or complicated where fluid reservoirs are located at greater distances from the flow cell as compared to the E4A or such reservoirs are larger than those used on the E4A. Electrical noise sources, such as stepper motors and solenoids, which could be place outside the Faraday shielding on the E4A may be very difficult to adequately shield on a larger instrument. Furthermore, each grounding bypass capacitor at a respective fluid reservoir becomes less effective as the associated fluid path is lengthened and/or interrupted by pinch valves or peristaltic pumps.

Thus, there is a need for an improved flow cell of the type described above which is less susceptible to noise entering the cell via the various fluid conduits connected thereto.

SUMMARY OF THE INVENTION

The present invention overcomes the limitations and drawbacks described above and provides an improved flow cell displaying dramatically reduced sensitivity to externally induced noise. In accordance with the present invention, a conductive member has at least portions thereof disposed within the sample fluid conduit proximate the electrochemically active tips of the ion selective electrodes and the salt bridge. As a further improvement, the solution ground is removed from the entrance of the reference fluid conduit and instead placed at the entrance of the acid diluent conduit into the cell. As yet a further improvement, capacitors may be connected at the inlets and outlets of each of the remaining conduits, thereby providing an AC path to ground for electrical noise carried by the fluid within the conduits. In the embodiment disclosed herein, the conductive member is preferably a metallic wire which may be, for example, gold, rhodium or platinum.

BRIEF DESCRIPTION OF THE FIGURES

FIG. 1A is a partial section view (section lines omitted for clarity) of the fluid conducting core of the flow cell of FIG. 1 taken along section line 1A of FIG. 1.

FIG. 2 illustrates a system incorporating the improved flow cell of FIG. 1.

DETAILED DESCRIPTION OF THE INVENTION

Figure 1:
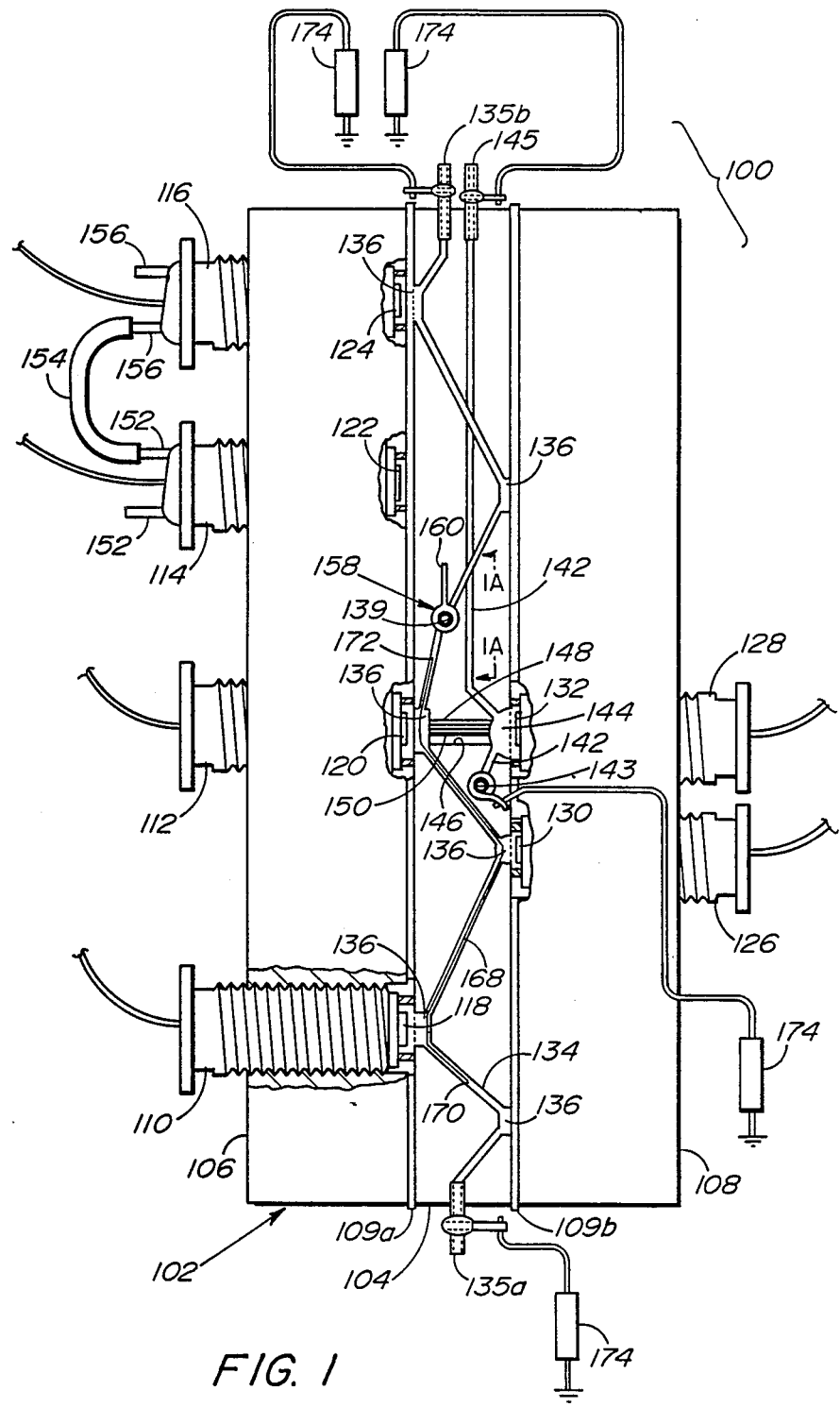
FIG. 1 illustrates an improved flow cell in accordance with the present invention.

With reference to FIG. 1, an improved electrochemical analysis flow cell 100 includes a body 102 which in turn comprises a central fluid conducting core 104 and electrode retaining side plates 106 and 108. The electrode retaining side plates 106 and 108 are removably affixed to the core 104 by suitable means such a screws (not shown). Rubber gaskets 109a and 109b provide a seal between the core 104 and side plates 106. The core 104 may be formed from a clear plastic material, allowing visual inspection of its internal structure as illustrated in FIG. 1, and the side plates 106 and 108 may be formed from an opaque plastic material.

Four ion selective electrodes 110, 112, 114 and 116 are threadably fixed into the side plate 106. Electrochemically active surfaces 118, 120, 122 and 124 of the respective electrodes 110, 112, 114 and 116 are disposed proximate a plane defined by the gasket 109a. Similarly, ion selective electrodes 126 and 128 are threadably secured within the side plate 108, each of such electrodes 126 and 128 carrying a respective electrochemically active surface 130 and 132 proximate a plane defined by the gasket 109b. In the embodiment disclosed herein, the electrodes 110 and 112 are potassium and chloride ion selective electrodes and the electrodes 126 and 128 are each sodium ion selective electrodes. The electrodes 110, 112, 126 and 128 have surfaces 118, 120, 130 and 132 of the type known in the art. Lastly, the electrodes 114 and 116 are electrodes adapted for measuring $CO_2$ similar to those described in U.S. Pat. No. 4,490,234 which is incorporated herein by reference.

A sample fluid conduit 134 is formed within the core 104. As seen with reference to the orientation of the cell 100 in FIG. 1, the sample conduit 134 enters the lower end of the core 104 via a metallic tubular fitting 135a and describes a zig-zag path within the core 104. The conduit 134 exits the top of the core 104 via a metallic tubular fitting 135b. The conduit 134 includes a plurality of cavities 136 formed at the planes defined by the gaskets 109a and 109b. Several of the cavities 136 are positioned to expose the electrochemically active surfaces 118, 120, 124, and 130 to fluid flowing through the sample conduit 134. The remaining cavities 136 serve as mixing chambers to help assure that the fluid flowing through the sample conduit is of a homogeneous composition as such fluid flows past the electrochemically active suraces 118, 130, 120, and 124. An acid diluent conduit 138 (FIG. 1A) enters the side of the core 104 via a metallic tubular fitting 139, intersecting the sample conduit 134 at an intersection 140 above the electrodes 112 and 128.

A reference solution conduit 142 enters the side of the core 104 via a metallic tubular fitting 143 generally between the electrodes 110 and 112. The fitting 143 is similar to the fittings 135a, 135b and 139. The reference conduit 142 includes a cavity 144 formed at the plane defined by the gasket 109b proximate the electrochemically active surface 132 to expose such surface to fluid flowing through the reference conduit 142. The reference conduit 142 is directed upwardly from the cavity 144 through the core 104, exiting the upper end (as illustrated with respect to the orientation of FIG. 1) of the core 104 via a metallic tubular fitting 145. As illustrated in FIGS. 1 and 1A, the reference conduit 142 describes a nonintersecting path past the sample conduit 134.

A bore 146 is formed within the core 104 between the cavity 136 adjacent the electrochemically active surface 120 and the cavity 144. Disposed within the bore 146 is a fluid-tight plug 148 through which passes an electrically conductive salt bridge 150. The salt bridge 150 provides a low impedance electrical connection between the cavity 136 proximate the surface 120 and the cavity 144. The salt bridge may comprise, for example, compressed fibers or porous ceramic, all well known in the art.

With continued reference to FIG. 1, a conduit 152 provides a buffer fluid path through the $CO_2$ reference electrode 114. The conduit 152 is connected via a flexible tube 154 to a conduit 156 which provides a fluid path through the measuring electrode 116. The conduits 152 and 156 allow circulation of alkaline buffer through both of the electrodes 114 and 116 as is described in U.S. Pat. No. 4,490,234 referenced above.

In accordance with the present invention, the cell 100 includes a solution ground 158. In the embodiment disclosed herein, the solution ground 158 comprises the fitting 139. A conductive wire 160 is soldered or braised to the fitting 139 and the wire 160 is in turn connected to instrument ground for the instrument (described more fully with reference to FIG. 2 below) which includes the flow cell 100. Such instrument ground, for example, provides the common or ground potential for the electronic circuitry within the instrument. As so positioned, the solution ground 158 is disposed in contact with a fluid flow path of homogeneous composition.

Further in accordance with the present invention a conductive member 168 is disposed within the sample conduit 134. A first end 170 of the conductive member 168 lies slightly upstream (fluid flow from the bottom of the cell 100 to the top of the cell 100 as seen in FIG. 1) from the surface 118 of the electrode 110. A second end 172 of the conductive member 168 lies between the surface 120 and the junction 140. The conductive member 168 provides a highly conductive path between the cavities 136 in which the electrochemically active surfaces 118, 130, and 120 are disposed and the salt bridge 150.

The conductive member 168 is electrically connected only to the fluid flowing through the sample conduit 134, that is, the conductive member 168 is not mechanically connected directly to any of the surfaces 118, 130, 120, the salt bridge 150 or the solution ground 158. Thus, the conductive member 168 is electrically free or floating within the sample conduit 134. The second end 172 is disposed such that the conductive member 168 is exposed to a fluid flowing in the sample conduit 134 prior to mixing with fluid flowing in the acid conduit 138. Thus, the conductive member 168 is disposed in a fluid flow path of essentially a homogeneous composition. In the embodiment disclosed herein, the conductive member 168 is preferably a gold wire with a diameter of approximately 0.005 inch. The diameter of the conductive member 168 is exaggerated in FIGS. 1 and 1A for clarity. Gold wire is selected for high conductivity, flexibility, corrosion resistance, and minimum physical interference with fluid flowing through the sample conduit 134. Other conductive materials such as low electrically resistant noble metals including rhodium and platinum are also suitable.

Further in accordance with the present invention, a plurality of capacitors 174 provide an AC bypass path between the remaining inlets and outlets of sample and reference conduits 134 and 142 and ground. One of the leads of the capacitors 174 is connected to the fittings 135a, 135b, 143 and 145. The other of the leads of each of the capacitors 174 is connected to instrument ground (illustrated schematically in FIG. 1) as described above with reference to the solution ground 158. In the embodiment disclosed herein, the capacitors are 470 picofarad polystyrene, 30 volt type, although other low leakage current type capacitors may be substituted as will be appreciated by those skilled in the art.

With reference now to FIG. 2, a system 200 including the cell 100 of the present invention comprises a sample delivery system 202 adapted to aspirate sample from a sample cup 204 or draw internal reference solution from an internal reference solution reservoir 206. A diluent delivery pump 208 draws diluent-buffer from a reservoir 210. The output of the diluent delivery pump 208 is connected with the output of the sample delivery system 202. With the sample delivery system 202 operating simultaneously with the diluent delivery pump 208, sample or internal reference solution delivered by the sample delivery system 202 is diluted with diluent-buffer provided by the pump 208. The diluted sample or internal reference solution is connected via a suitable conduit to the sample conduit 134.

Internal reference solution is also pumped from the reservoir 206 by a peristaltic pump 212 and delivered to the reference solution conduit 142. Fluid flowing out of the sample and reference conduits 134 and 142 is conducted via drain lines 214 to a waste reservoir 216.

Acid diluent from an acid diluent reservoir 218 is pumped via an acid diluent delivery pump 220 to the conduit 138 (FIG. 1A) in the flow cell 100. The acid diluent mixes with the fluid flowing in the sample conduit 134 at the intersection 140. The mixture continues past the $CO_2$ measuring electrode 116. Alkaline buffer for the $CO_2$ reference electrode 114 and measuring electrode 116 is supplied from an alkaline buffer reservoir 222 via peristaltic pump 223 to the conduit 152. The conduit 156 is connected by a suitable drain tubing to the waste reservoir 216. A solution ground 224 may be included near the conduit 152. The solution ground 224 may take the form of a conductive metallic tube inserted into the conduit leading from the pump 223 to the conduit 152. Similarly, a capacitor 225 may be connected between system ground and the fluid line connected to the conduit 156. The capacitor 225 may be similar to the capacitors 174.

The output of the compensating electrode 128 is connected via a suitably shielded wire to inputs of three differential amplifiers 226, 228 and 230. The other inputs of differential amplifiers 226, 228 and 230 are connected via shielded wires to the ion selective electrodes 126, 110 and 112, respectively. The differential amplifiers 226, 228 and 230 develop outputs that are proportional to the difference of the signals applied thereto and such outputs are applied to analog-to-digital converters (ADCs) 232, 234 and 235 which in turn develop a digital output proportional to the analog signal applied thereto. The digital outputs are applied to a microcomputer 236. The outputs of the reference and measuring $CO_2$ electrodes 114 and 116 are also applied to a differential amplifier 238, the output of which is applied to an analog-to-digital converter (ADC) 240. The output of the ADC 240 is applied to the microcomputer 236. The microcomputer 236 calculates analyte concentrations and displays such concentrations on a suitable display 242 all in a fashion known in the art.

It is to be recognized that, except for the improved flow cell 100 as described above, the system 200 of FIG. 2 is an otherwise conventional clinical analytical instrument employing non-segmented fluid flow cell technology such as, for example, Beckman's E4A Analyzer described above in the Background of the Invention. The system 200 may be advantageously a system that is physical larger than the E4A, with corresponding longer fluid paths leading to and from the flow cell 100 and larger fluid reservoirs.

In general operation, diluted reference solution is flowed through the sample conduit 134 by means of the sample delivery system 202 and the diluent delivery pump 208 to provide reference measured values from each of the electrodes 110, 112, 116 and 126. Simultaneously, reference solution flows through the reference conduit 142 via the pump 212 and is sensed by the compensating electrode 128. The differences between the signals developed by the compensating electrode 128 and the electrodes 110, 112 and 126 provide reference or standard measurement values which compensate for system drift between calibrations of the system 200.

Acid diluent from the reservoir 218 flows through the acid conduit 138 and mixes with the fluid in the conduit 134 at the intersection 140, thereafter flowing past the electrode 116 which, with the reference electrode 114, operate as is described in U.S. Pat. No. 4,490,234.

After the reference solution measurements have been made, fluid containing sample from the sample delivery system 202 mixed with diluent buffer from the pump 208 flows through the sample conduit 134 and mixes with acid diluent flowing through the conduit 138. Electrodes 110, 112, 116 and 126 measure the ion concentrations of the analytes within the sample and such measurements are converted into analyte concentrations in a manner well known in the art.

In the system 200, the reference and sample measurements are made in an alternating fashion, that is, reference, sample, reference, sample, and so on. Furthermore, the system is periodically calibrated. A calibrator reagent is substituted for sample and is processed to provide calibration values which are used by the microprocessor 236 in a conventional fashion.

The improvements embodied in flow cell 100 of the present invention advantageously reduce externally induced noise and interference which would otherwise influence measurements made with a prior art flow cell as is described in the Background of the Invention.

More particularly, by connecting the solution ground 158 at the fluid inlet of the acid conduit 138, solution ground is not applied directly to the compensating electrode 128 as done with the prior art flow cell described above. In such prior art flow cell, electrical noise and interference in the sample conduit is conducted via the salt bridge to the reference conduit but is largely shunted to instrument ground via the reference fluid flowing in the reference solution conduit. Accordingly, the compensating electrode in the prior art flow cell does not detect such noise and interference or does so to only a limited extent. Since the noise and interference is detected by the measuring electrodes but is not detected by the compensating electrode or is detected by the compensating electrode 128 to only a limited extent, the electrical noise and interference detected by the measuring electrodes in the prior art flow cell produces corresponding measurement errors.

In accordance with the present invention, however, the solution ground 158 comprises the fitting 139 at the inlet of the acid conduit 138. Thus, electrical noise or interference present in the sample conduit 134 at the salt bridge 150 and which may be detected to varying degrees by the electrodes 110, 112 and 126 is also conducted by the salt bridge 150 to the compensating electrode 128. The compensating electrode 128 detects the electrical noise presented to it by the salt bridge 150 and applies such detected noise and interference to the differential amplifiers 226, 228 and 230, thereby reducing the effect of the noise and interference detected by the electrodes 110, 112 and 126.

With respect to the conductive member 168, external electrical noise may generate electrical currents that are conducted into the cell 100 via the fluid conduits connected thereto. Fluid within the various lengths of conduits within the flow cell 100 present some impedance to such current flow. Accordingly, absent the conductive member 168, gradient potentials or voltages would be generated, for example, within the conduit 134 between the electrodes 110, 126 and 112. Such gradient potentials would vary between the electrodes 110, 126 and 112 according to the direction of the current flow and the fluid impedances presented along the respective fluid paths. In the prior art flow cell described in the Background of the Invention above, these gradient potentials would be sensed by the measuring electrodes, introducing corresponding measurement errors.

In accordance with the present invention, however, the conductive member 168 provides a highly conductive electrical path between the cavities 136 in which the electrochemically active surfaces 118, 130 and 120 and one end of the salt bridge 150 are disposed. The conductive member 168 averages externally induced noise along its length. As a consequence, all of the surfaces 118, 120 and 130 experience essentially the identical average voltage resulting from external noise- and interference-induced current flow. This same average potential is also presented to the salt bridge by the conductive member 168 and is conducted via the salt bridge 150 to and sensed by the compensating electrode 128. The average potential is substantially eliminated when the difference between the output of the compensating electrode 128 and the outputs of the respective electrodes 110, 112 and 126 are processed by the respective differential amplifiers 226, 228 and 230. Accordingly, gradient potential differences which would otherwise produce measurement errors in the prior art flow cell are substantially reduced or eliminated.

Furthermore, the bypass capacitors 174 provide yet an additional bypass path for AC noise which might otherwise be conducted into the cell 100. The bypass capacitors 174 further enhance the improvements just described and together represent a substantial improvement over the prior art, enabling greatly improved signal-to-noise ratio measurements to be obtained.

It is to be recognized that various modifications to the present invention may be made. For example, the conductive member 168 may take the form of a conductive material plated or deposited on the walls of the conduit 134. The plating is deposited in the conduit 134 proximate the surfaces 118, 120 and 130 and in the portion of the conduit 134 through which homogeneous fluid flows. Furthermore, if the chemical composition of the fluids flowing between a solution ground 158 and the end 170 is homogeneous, the conductive member 168 may be connected to the solution ground 158. Alternately, the conductive member 168 or its equivalent can be directly connected to instrument ground via a conductor which passes through a side of the core 104 and directly connects to the conductive member 168. A suitable seal, such as silicone rubber, would seal the conductor in the core to prevent fluid leakage. Furthermore, the conductor may be an extension of the conductive member 168 itself which is brought out through a side of the core 104 to a suitable connection point. A further alternative is the use of separate conductors each passing through a side of the core 104, one end of the separate conductors terminating in the cavities 136 in which the surfaces 118, 130 and 120 and one end of the salt bridge 150 are disposed. The other ends of such separate conductors are then connected together outside of the core 104 by a suitable conductor. Such an embodiment may be particularly useful where the ion selective electrodes are in separate individual flow chambers that are interconnected by suitable tubing or the like.

Other alternatives will be readily apparent to those skilled in the art. In each instance, a highly conductive path is established between the cavities in a homogeneous flow path in which electrochemically active surfaces of ion selective electrodes are disposed. The highly conductive path is also established to a cavity in the homogeneous flow path in which a salt bridge to the reference solution conduit is disposed.

It is to be recognized that the present invention is not to be limited to the specific embodiment disclosed herein, but is instead defined by the full scope of the following claims and all equivalents thereto.

I claim:

1. An improved ion selective electrode flow cell comprising:
   a first fluid conduit;
   at least two ion sensing electrodes each having an ion sensing surface disposed within the first fluid conduit;
   a second fluid conduit;
   an ion sensing electrode having an ion sensing surface disposed within the second conduit;
   an electrically conducting bridge connecting the first and second fluid conduits; and
   a conductive member other than electrodes, having at least portions thereof disposed in the first fluid conduit proximate the ion sensing surfaces of the at least two ion sensing electrodes and the bridge.

2. A flow cell as in claim 1 wherein the flow cell further includes a third fluid conduit intersecting the first fluid conduit; and
   grounding means for grounding fluid flowing through the third fluid conduit.

3. A flow cell as in claim 2 wherein the cell includes capacitor means connected between ground and entry and exit ports of each of the first and second fluid conduits.

4. A flow cell as in claim 1 wherein the conductive member comprises a conducting metallic wire disposed in the first fluid conduit.

5. A flow cell as in claim 4 wherein the material comprising the conductive metallic wire is selected from a group including gold, platinum and rhodium.

6. A flow cell as in claim 1 wherein the conductive member includes conductive metallic plating deposited on the first fluid conduit.

7. A flow cell as in claim 1 further including means for grounding the first conduit at a point along the first fluid conduit proximate the conductive member.

8. A flow cell as in claim 1 further including means for providing a low impedance path from the conductive member to ground.

9. An improved ion selective electrode flow cell comprising:
   a flow cell body;
   a first fluid conduit formed in the flow cell body;
   at least two ion sensing electrodes each having an ion sensing surface disposed within the first fluid conduit;
   a second fluid conduit formed in the flow cell body;
   a compensating ion sensing electrode having an ion sensing surface disposed within the second conduit;
   an electrically conducting bridge connecting the first and second fluid conduits; and
   a conductive member, other than the electrodes, disposed within the first fluid conduit and extending within the first fluid conduit along a path proximate the ion sensing surface of the at least two ion sensing electrodes and the bridge.

10. A flow cell as in claim 9 further including means for providing a low impedance path from the conductive member for grounding the conductive member.

11. An improved ion selective electrode flow cell comprising:
   a flow cell body;
   a first fluid conduit formed in the flow cell body;

at least two ion sensing electrodes each having an ion sensing surface disposed within the first fluid conduit;

a second fluid conduit formed in the flow cell body;

a compensating ion sensing electrode having an ion sensing surface disposed within the second conduit;

an electrically conducting bridge connecting the first and second fluid conduits;

a conductive member, other than electrodes, disposed within the first fluid conduit and extending within the first fluid conduit along a path proximate the ion sensing surface of the at least two ion sensing electrodes and the bridge;

a third fluid conduit formed in the flow cell body and intersecting the first fluid conduit proximate the conductive member; and grounding means for grounding the third fluid conduit.

12. An improved ion selective electrode flow cell comprising:

a first fluid conduit;

at least two ion sensing electrodes each having an ion sensing surface disposed within the first fluid conduit;

a second fluid conduit without grounding means for fluid flowing through the second fluid conduit;

an ion sensing electrode having an ion sensing surface disposed within the second conduit;

a conductive member, other than the electrodes, having at least portions thereof disposed in the first fluid conduit proximate to the ion sensing surfaces of the at least two ion sensing electrodes and the bridge;

a third fluid conduit intersecting the first fluid conduit; and grounding means for grounding fluid flowing through the third fluid conduit.

13. A flow cell as in claim 12 wherein the cell includes capacitor means connected between ground and entry and exit ports of each of the first and second fluid conduits.

14. A flow cell as in claim 12 wherein the conductive member comprises a conducting metallic wire disposed in the first fluid conduit.

15. A flow cell as in claim 14 wherein the material comprising the conductive metallic wire is selected from a group including gold, platinum and rhodium.

16. A flow cell as in claim 14 wherein the conductive member includes conductive metallic plating deposited on the first fluid conduit.

17. A flow cell as in claim 12 further including means for grounding the first conduit at a point along the first fluid conduit proximate the conductive member.

* * * * *

UNITED STATES PATENT AND TRADEMARK OFFICE
CERTIFICATE OF CORRECTION

PATENT NO. : 4,889,611
DATED : 12/26/39
INVENTOR(S) : William H. Blough, Jr.

It is certified that error appears in the above-identified patent and that said Letters Patent is hereby corrected as shown below:

In printed patent: column 3, line 1 and 2 currently reads "electrodes 110, 112, and 126 have surfaces 118, 120, 130 and 132 of the type known in the art." should read "electrodes 110, 112, 126 and 128 have glass, PVC or silver-silver chloride pellet tips or surfaces 118, 120, 130 and 132 of the type known in the art."

Signed and Sealed this

Twenty-first Day of May, 1991

Attest:

HARRY F. MANBECK, JR.

Attesting Officer

Commissioner of Patents and Trademarks